United States Patent
Zajac

(10) Patent No.: US 9,839,462 B2
(45) Date of Patent: Dec. 12, 2017

(54) SURGICAL CUTTING BLOCK

(71) Applicant: ARTHREX, INC., Naples, FL (US)

(72) Inventor: Eric Zajac, Naples, FL (US)

(73) Assignee: ARTHREX, INC., Naples, FL (US)

(*) Notice: Subject to any disclaimer, the term of this patent is extended or adjusted under 35 U.S.C. 154(b) by 509 days.

(21) Appl. No.: 13/741,413

(22) Filed: Jan. 15, 2013

(65) Prior Publication Data

US 2013/0204257 A1    Aug. 8, 2013

Related U.S. Application Data

(60) Provisional application No. 61/595,373, filed on Feb. 6, 2012.

(51) Int. Cl.
| | |
|---|---|
| A61F 5/00 | (2006.01) |
| A61B 17/88 | (2006.01) |
| A61B 17/15 | (2006.01) |

(52) U.S. Cl.
CPC ........ *A61B 17/8863* (2013.01); *A61B 17/155* (2013.01)

(58) Field of Classification Search
CPC . A61B 17/155; A61B 17/154; A61B 17/8863; A61B 17/157; A61B 17/158
USPC ........................................... 606/86 R, 87–89
See application file for complete search history.

(56) References Cited

U.S. PATENT DOCUMENTS

| | | |
|---|---|---|
| 5,683,398 A | 11/1997 | Carls et al. |
| 5,720,752 A * | 2/1998 | Elliott et al. ............... 606/88 |
| 6,258,095 B1 | 7/2001 | Lombardo et al. |
| 6,673,116 B2 * | 1/2004 | Reiley .................... 623/21.18 |
| 7,572,261 B2 * | 8/2009 | Collazo ..................... 606/87 |
| 2003/0100906 A1 | 5/2003 | Rosa et al. |
| 2004/0260301 A1* | 12/2004 | Lionberger et al. .......... 606/88 |
| 2007/0270872 A1 | 11/2007 | Thau et al. |
| 2008/0015605 A1* | 1/2008 | Collazo ..................... 606/87 |
| 2008/0195109 A1* | 8/2008 | Hunter et al. ............... 606/87 |
| 2008/0228189 A1* | 9/2008 | Fox et al. .................. 606/88 |
| 2009/0082774 A1 | 3/2009 | Oti et al. |
| 2009/0093816 A1* | 4/2009 | Roose et al. ............... 606/87 |
| 2011/0046629 A1 | 2/2011 | Green, II et al. |

OTHER PUBLICATIONS

Extended European Search Report for Application No. EP 13 15 2901 dated Apr. 16, 2013.

* cited by examiner

*Primary Examiner* — Si Ming Ku
(74) *Attorney, Agent, or Firm* — Karish & Bjorgum, PC

(57) ABSTRACT

A surgical cutting block according to an exemplary aspect of the present disclosure includes, among other things, a block body including a top surface having a first thickness that extends between a first surface and an opposing second surface of the block body and a capture disposed at the top surface. The capture includes a second thickness that is less than the first thickness of the top surface.

19 Claims, 4 Drawing Sheets

SURGICAL CUTTING BLOCK

CROSS-REFERENCE TO RELATED APPLICATION

This application claims priority to U.S. Provisional Application No. 61/595,373, which was filed Feb. 6, 2012.

BACKGROUND

This disclosure relates to orthopedic surgical instrumentation, and more particularly to a surgical cutting block for preparing a bone to receive a prosthetic implant, such as a total knee implant.

Total or partial knee replacement surgery has been performed for many years to treat patients with diseased knee joints. Some knee instrumentation sets include cutting blocks that can be used to make a variety of cuts (i.e., resections) in a patient's bone to prepare the bone for receiving a prosthetic implant. For example, a 4-in-1 cutting block can be used to make anterior, posterior and chamfer cuts to prepare a femur for accepting a total knee implant.

A variety of different types of cutting blocks are known, and surgeon preference for the different types of cutting blocks can vary. For example, some surgeons may prefer "open" cutting blocks that allow the surgeon to control the cutting angle of the cuts, while other surgeons may prefer "slotted" cutting blocks that limit the ability to increase and/or decrease the angle of the cuts. As a result, a surgical institution may have to maintain a relatively large inventory of surgical instrumentation to satisfy the different preferences of its surgeons.

SUMMARY

A surgical cutting block according to an exemplary aspect of the present disclosure includes, among other things, a block body including a top surface having a first thickness that extends between a first surface and an opposing second surface of the block body and a capture disposed at the top surface. The capture includes a second thickness that is less than the first thickness of the top surface.

In a further non-limiting embodiment of the foregoing surgical cutting block, the first surface extends obliquely relative to the opposing second surface.

In a further non-limiting embodiment of either of the foregoing surgical cutting blocks, the first surface is non-parallel to the opposing second surface.

In a further non-limiting embodiment of any of the foregoing surgical cutting blocks, the capture extends from the top surface in a direction opposite from a bottom surface of the block body.

In a further non-limiting embodiment of any of the foregoing surgical cutting blocks, the capture is integrally formed with the block body.

In a further non-limiting embodiment of any of the foregoing surgical cutting blocks, the capture is a separate component from the block body.

In a further non-limiting embodiment of any of the foregoing surgical cutting blocks, the capture is magnetically connected to the top surface.

In a further non-limiting embodiment of any of the foregoing surgical cutting blocks, the capture includes a slot.

In a further non-limiting embodiment of any of the foregoing surgical cutting blocks, at least one posterior cutting guide slot is adjacent to a bottom surface of the block body.

In a further non-limiting embodiment of any of the foregoing surgical cutting blocks, at least one chamfer cutting guide slot extends through the block body.

In a further non-limiting embodiment of any of the foregoing surgical cutting blocks, the second thickness is approximately half of the first thickness.

In a further non-limiting embodiment of any of the foregoing surgical cutting blocks, the second thickness is between 40% and 60% of the first thickness.

A method for resectioning a bone according to another exemplary aspect of the present disclosure includes, among other things, positioning a surgical cutting block relative to a bone, inserting a cutting tool through a capture of the surgical cutting block, positioning the cutting tool at a desired angle relative to the bone and resectioning a portion of the bone using the cutting tool.

In a further non-limiting embodiment of the foregoing method for resectioning a bone, the step of positioning the cutting tool includes angling the cutting tool in the anterior direction relative to a horizontal plane of a top surface of the surgical cutting block.

In a further non-limiting embodiment of either of the foregoing methods for resectioning a bone, the method comprises the step of visualizing the cutting tool at an interface between the bone and the surgical cutting block subsequent to the step of inserting the cutting tool through the capture.

In a further non-limiting embodiment of any of the foregoing methods for resectioning a bone, the method comprises the step of attaching the capture to a top surface of the surgical cutting block subsequent to the step of positioning the surgical cutting block.

In a further non-limiting embodiment of any of the foregoing methods for resectioning a bone, the capture is magnetically attached to the top surface.

In a further non-limiting embodiment of any of the foregoing methods for resectioning a bone, the capture includes a second thickness that is less than a first thickness of a top surface of the surgical cutting block.

In a further non-limiting embodiment of any of the foregoing methods for resectioning a bone, the method comprises the step of making a posterior cut in the bone by inserting the cutting tool through a posterior cutting guide slot of the surgical cutting block.

In a further non-limiting embodiment of any of the foregoing methods for resectioning a bone, the method comprises the step of making a chamfer cut in the bone by inserting the cutting tool through a chamfer cutting guide slot of the surgical cutting block.

BRIEF DESCRIPTION OF THE DRAWINGS

The various features and advantages of this disclosure will become apparent to those skilled in the art from the following detailed description. The drawings that accompany the detailed description can be briefly described as follows.

DETAILED DESCRIPTION

Figure 1:
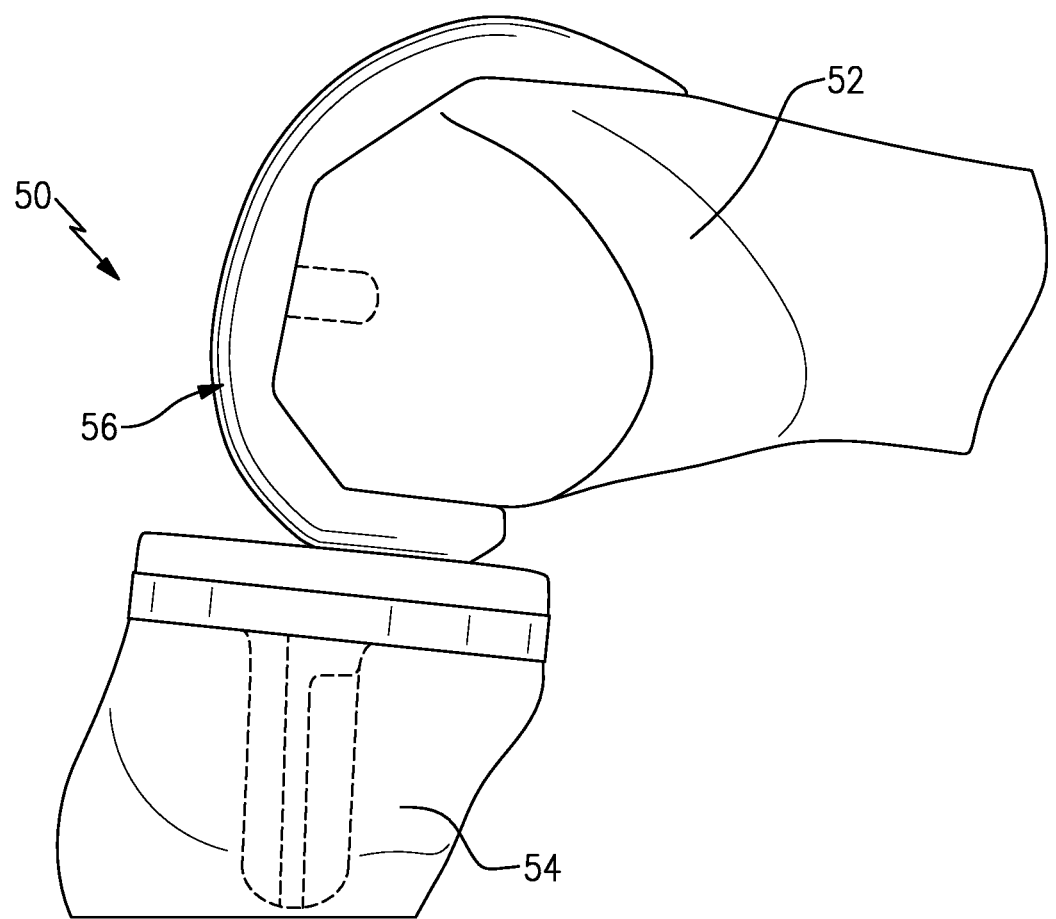
FIG. 1 schematically illustrates a joint having a prosthetic implant.
Figure 2:
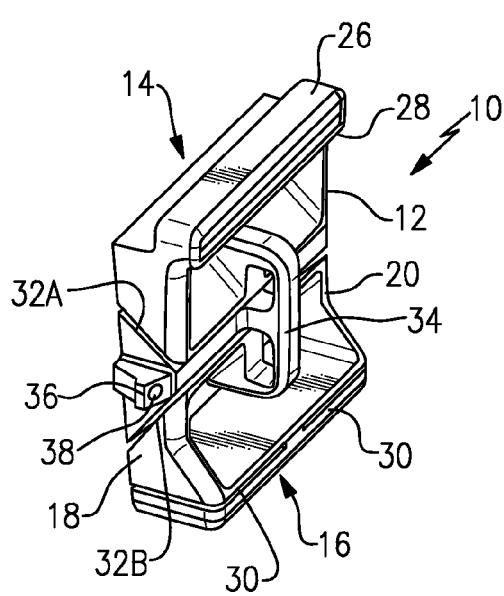
FIG. 2 illustrates a surgical cutting block that can be used to make a variety of cuts in a bone to prepare the bone for receiving a prosthetic implant.
Figure 3:
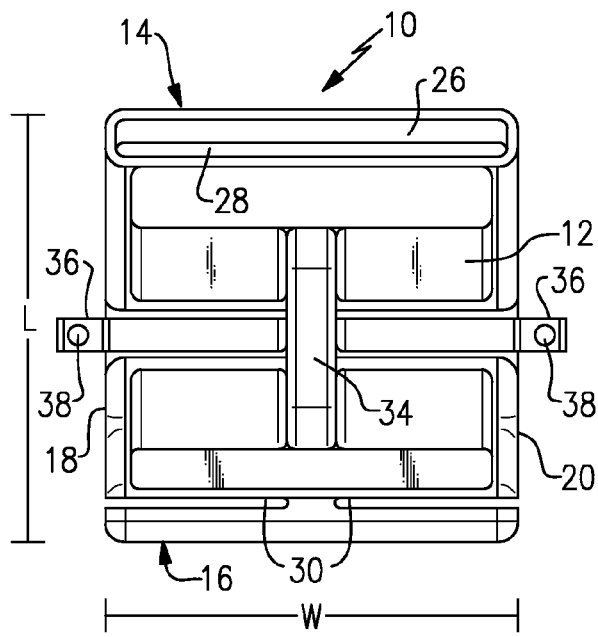
FIG. 3 is a front view of the surgical cutting block of FIG. 2.
Figure 4:
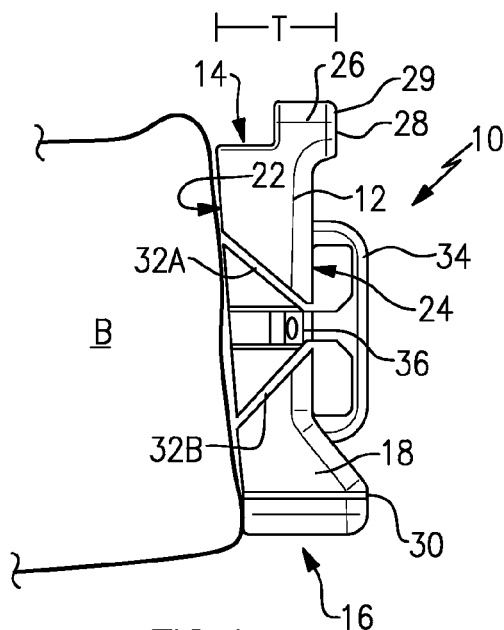
FIG. 4 is a side view of the surgical cutting block of FIG. 2.
Figure 5:
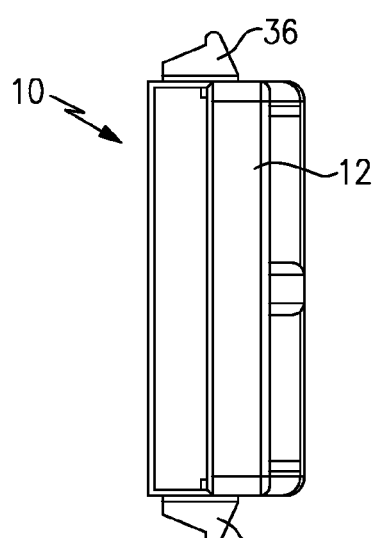
FIG. 5 is another view of the surgical cutting block of FIG. 2.

FIG. 1 illustrates a joint 50, such as a knee joint of the human body that extends between a femur 52 and a tibia 54. Diseased portions of the femur 52 and the tibia 54 have been removed and replaced with a prosthetic implant 56 that is positioned within the joint 50. In the exemplary embodiment, the prosthetic implant 56 is a total joint implant, such as a total knee implant, although other prosthetic implants could also benefit from the various teachings of this disclosure. Various orthopedic surgical instruments can be used to prepare the femur 52 and/or tibia 54 for the implantation of the prosthetic implant 56. Examples of orthopedic surgical instruments that can be used for this purpose are detailed below.

FIGS. 2 through 5 illustrate an exemplary surgical cutting block 10 that can be used to prepare a bone B (See FIG. 4) to receive a prosthetic implant. In this exemplary embodiment, the surgical cutting block 10 is part of a total joint instrument set that can be used to prepare a patient's femur for accepting a total knee implant. For example, the surgical cutting block 10 can be used to resection a patient's femur by making anterior, posterior and chamfer cuts in the femur. Various other guides and instruments may be required to prepare the bone for receiving, positioning and using the surgical cutting block 10 to make the anterior, posterior and chamfer cuts. It should be understood that the surgical cutting block 10 could also be used for additional purposes related to any bone, total joint implant and/or any other surgery.

The surgical cutting block 10 includes a block body 12 having a length L that extends between a top surface 14 and a bottom surface 16. A width W of the block body 12 extends between opposing sides 18, 20 (see FIG. 3). A thickness T of the block body 12 extends between a first surface 22 (that faces a bone B of the patient) and an opposing second surface 24 that is positioned on an opposite side of the block body 12 from the first surface 22, i.e., towards a surgeon or other user of the surgical cutting block 10 (see FIG. 4).

The first surface 22 may provide a flat surface for interfacing with the bone B. In one example, the first surface 22 obliquely extends between the top surface 14 and the bottom surface 16 and is non-parallel to the opposing second surface 24. The size of the surgical cutting block 10 can vary depending on the size of the patient and could be provided in multiple sizes that correspond to different sizes of the prosthetic implant to be implanted. A sizing guide (not shown) can also be used to determine the appropriate size of the prosthetic implant prior to preparing the bone B for receiving the prosthetic implant.

The surgical cutting block 10 can include a capture 26 disposed at or adjacent to the top surface 14. In this exemplary embodiment, the capture 26 extends from the top surface 14 in a direction opposite from the bottom surface 16 and is integrally formed with the block body 12. However, the capture 26 could also be a separate component from the block body 12 (see FIG. 8). In one embodiment, a forward face 29 of the capture 26 extends axially forward of the opposing second surface 24 in a direction that extends away from the first surface 22.

The capture 26 includes a slot 28 that can receive a cutting tool (See FIGS. 7A and 7B), such as an oscillating saw or other suitable cutting tool, that can be inserted through the slot 28 to make an anterior cut in the bone B. In other words, the capture 26 and slot 28 provide a surgeon with a guide surface for performing a resection at a desired location of the bone B. In one embodiment, the slot 28 is a closed slot that extends across a width that is nearly the same as the width W of the block body 12. However, the size, shape and configuration of the slot 28 can vary.

The block body 12 of the surgical cutting block 10 can also include one or more posterior cutting guide slots 30. In the exemplary embodiment of FIGS. 2-5, the surgical cutting block 10 includes two posterior cutting guide slots 30 positioned adjacent to the bottom surface 16 of the block body 12. The posterior cutting guide slots 30 generally extend between the first surface 22 and the opposing second surface 24. In this embodiment, the posterior cutting guide slots 30 open into the opposing sides 18, 20 of the block body 12. The posterior cutting guide slots 30 receive a cutting tool and provide a guide surface for making posterior cuts with the cutting tool at a desired location of the bone B.

One or more chamfer cutting guide slots 32A, 32B that provide guide surfaces for making chamfer cuts in the bone B can be disposed through the block body 12 of the surgical cutting block 10. In one embodiment, the chamfer cutting guide slots 32A, 32B are disposed longitudinally between the slot 28 of the capture 26 and the posterior cutting guide slots 30. The chamfer cutting guide slots 32A, 32B can be disposed at an angle through the block body 12. That is, the chamfer cutting guide slots 32A, 32B extend obliquely between the first surface 22 and the opposing second surface such that a transverse cut can be made in the bone B. In one exemplary embodiment, the chamfer cutting guide slot 32A can receive a cutting tool to make anterior chamfer cuts into the bone B, while the chamfer cutting guide slot 32B can be utilized to make posterior chamfer cuts in the bone B.

The surgical cutting block 10 can further include a handle 34 for maneuvering and positioning the surgical cutting block 10 relative to a patient's bone B. One or more engagement features 36 can extend from the opposing sides 18, 20 of the block body 12 and can be used to position and mount the surgical cutting block 10 relative to the bone B. The engagement features 36 may include openings 38 for receiving pins or other fasteners to removably mount the surgical cutting block 10 to the bone B so that the surgical cutting block 10 is securely affixed for resectioning the bone B. Alternatively, the engagement features 36 could include bone spikes that are driven into the bone B to removably secure the surgical cutting block 10 to the bone B.

Figure 6:
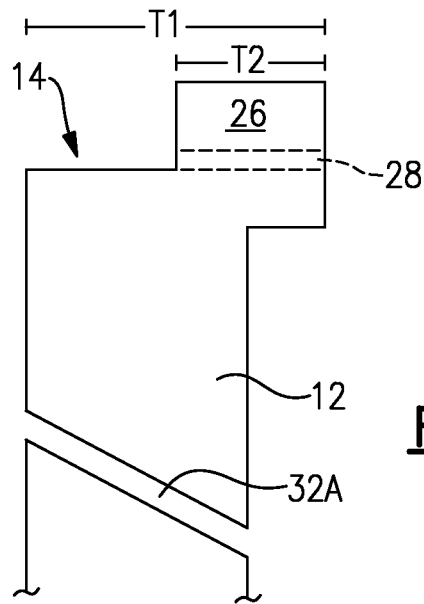
FIG. 6 illustrates a portion of the surgical cutting block of FIG. 2.

Referring to FIG. 6, the capture 26 of the surgical cutting block can include a second thickness T2 that is less than a first thickness T1 of the top surface 14 of the surgical cutting block 10. It should be understood that this view is not necessarily to the scale it would be in practice. In one exemplary embodiment, the second thickness T2 of the capture 26 is approximately half of the first thickness T1 of the top surface 14. In another example, the thickness T2 is between 40% and 60% of the first thickness T1. However, the second thickness T2 of the capture 26 could be any thickness that is less than the first thickness T1 of the top surface 14.

Figure 7A:
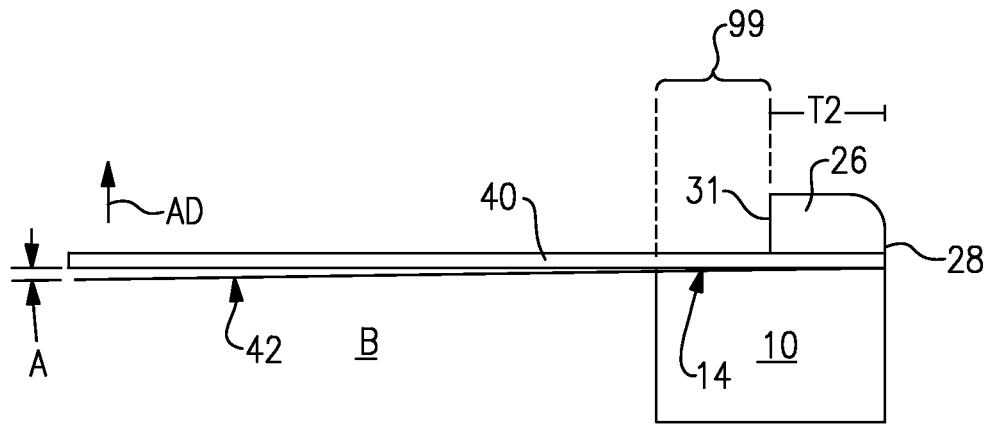
FIGS. 7A and 7B illustrate the use of a cutting tool with a surgical cutting block according to one embodiment of this disclosure.
Figure 7B:
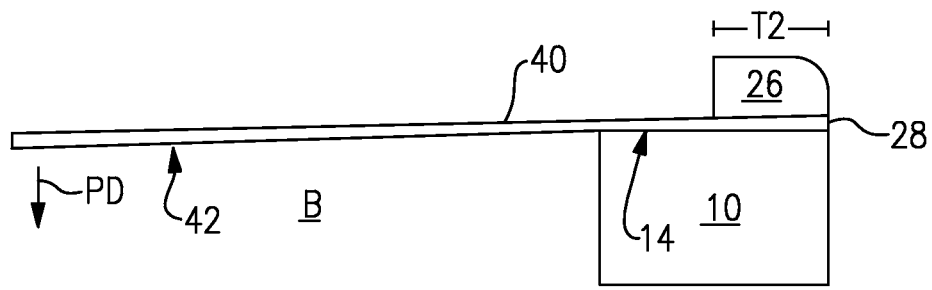

FIGS. 7A and 7B, with continued reference to FIGS. 1-6, schematically illustrate a method of resectioning a bone using a surgical cutting block, such as the surgical cutting block 10. The surgical cutting block 10 may first be positioned relative to a bone B. A cutting tool 40 can next be received through the slot 28 of the capture 26 of the surgical cutting block 10. The cutting tool 40 could include an oscillating saw blade or any other suitable cutting tool.

The cutting tool 40 can be inserted through the slot 28 and across the top surface 14 to create an anterior cut in the bone B, such as in a femur. The top surface 14 of the surgical cutting block 10 extends in a horizontal plane 42. The cutting tool 40 can be angled in an anterior direction AD (i.e., away from the center of the bone B) to position the cutting tool 40 at a desired angle relative to the bone B. The reduced second thickness T2 of the capture 26 enables the cutting tool 40 to be angled at an angle A relative to the horizontal plane 42 to improve the positioning of the cutting tool 40 relative to the bone B. In one exemplary embodiment, the cutting tool 40 can be angled any angle in the anterior direction AD that is less than or equal to 4° from the horizontal plane 42.

Once a desired angle has been established, the cutting tool 40 can be used to resection the bone B. The cutting tool 40 can additionally be used to make additional cuts in the bone B through the posterior cutting guide slots 30 and the chamfer cutting guide slots 32A, 32B of the surgical cutting block 10.

A surgeon has improved visualization of the cutting tool 40 at the interface between the bone B and the surgical cutting block 10 because the second thickness T2 of the capture 26 is less than the first thickness T1 of the top surface 14. For example, the cutting tool 40 is exposed to view from above in a visualization area 99 of the surgical cutting block 10 that extends between a rear face 31 of the capture 26 and the first surface 22 of the block body 12. The reduced second thickness T2 of the capture 26 also enables slight angling of the cutting tool 40 for improved surgical use that avoids any partial notching to the bone B. Also, as shown in FIG. 7B, the cutting tool 40 is substantially prevented from being angled in a posterior direction PD (i.e., toward the center of the bone B) relative to the horizontal plane 42 of the top surface 14.

Figure 8:
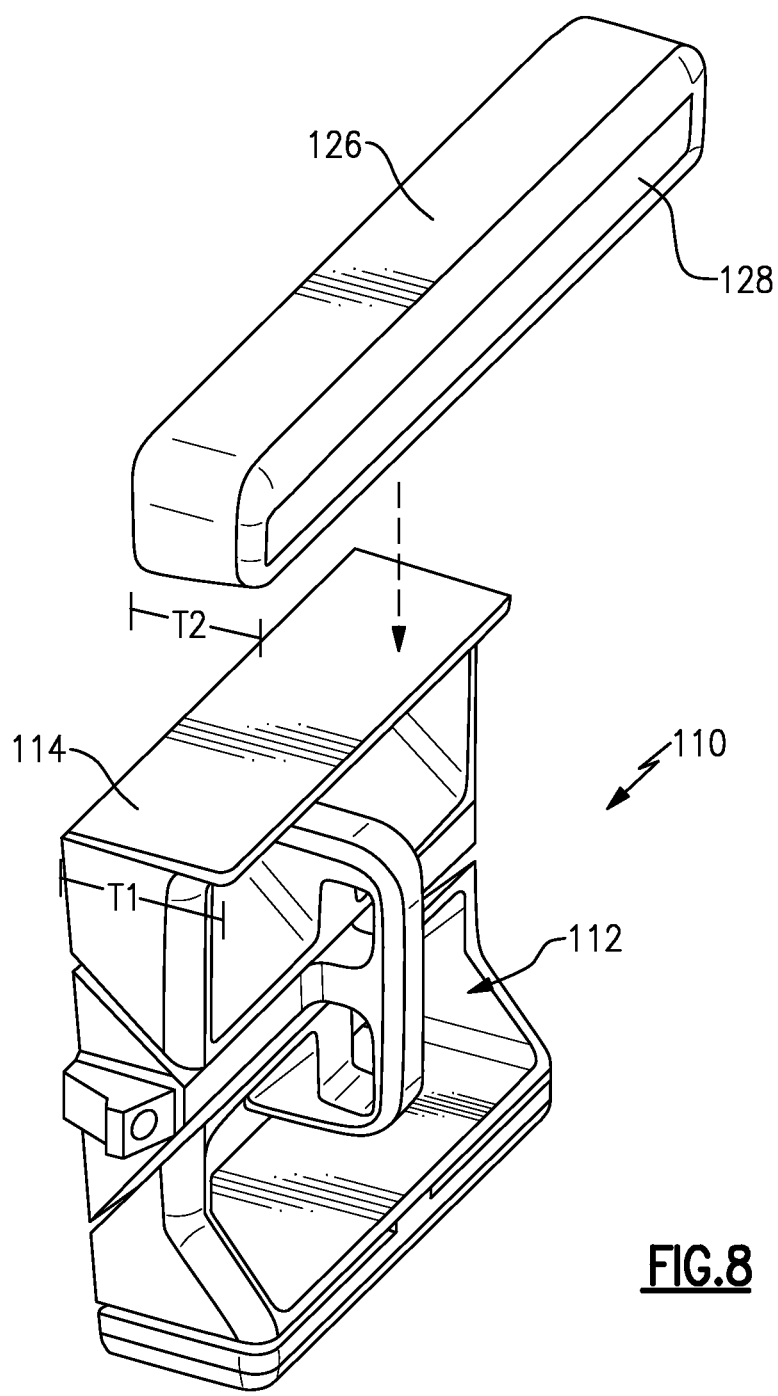
FIG. 8 illustrates another embodiment of a surgical cutting block.

FIG. 8 illustrates another exemplary surgical cutting block 110. In this disclosure, like reference numerals indicate similar features, whereas reference numerals with an added prefix numeral of "1" indicates slightly modified features. The surgical cutting block 110 of this exemplary embodiment includes a block body 112 and a capture 126 that is a separate component from the block body 112. In other words, the surgical cutting block 110 can embody a modular design that allows improved visualization of a cut location of a bone subsequent to positioning the surgical cutting block 110 relative to the bone and prior to attaching the capture 126 to the block body 112. The capture 126 can be mounted to a top surface 114 of the block body 112. The capture 126 can be mounted relative to the top surface 114 in any known manner to provide a guide surface for making an anterior cut in a bone. In one non-limiting embodiment, the capture 126 is magnetically connected to the top surface 114 of the surgical cutting block 110.

The capture 126 includes a slot 128 that can receive a cutting tool for performing cuts in a patient's bone. The capture 126 extends across a second thickness T2 that is less than a first thickness T1 of the top surface 114 of the block body 112.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical cutting block, comprising:
   a block body including a top surface, said block body including a first thickness that extends between a first surface and an opposing second surface of said block body, said first surface adapted to be received against an exterior surface of a bone;
   a capture disposed at said top surface, wherein said capture includes a second thickness that is less than said first thickness of said block body at said top surface and a slot that extends through said capture across an entirety of said second thickness; and
   at least one chamfer cutting guide slot that extends through said block body.

2. The surgical cutting block as recited in claim 1, wherein said first surface extends obliquely relative to said opposing second surface.

3. The surgical cutting block as recited in claim 1, wherein said first surface is non-parallel to said opposing second surface.

4. The surgical cutting block as recited in claim 1, wherein said capture extends from said top surface in a direction opposite from a bottom surface of said block body.

5. The surgical cutting block as recited in claim 1, wherein said capture is integrally formed with said block body.

6. The surgical cutting block as recited in claim 1, wherein said capture is a separate component from said block body.

7. The surgical cutting block as recited in claim 6, wherein said capture is magnetically connected to said top surface.

8. The surgical cutting block as recited in claim 1, comprising at least one posterior cutting guide slot adjacent to a bottom surface of said block body.

9. The surgical cutting block as recited in claim 1, wherein said second thickness is approximately half of said first thickness.

10. The surgical cutting block as recited in claim 1, wherein said second thickness is between 40% and 60% of said first thickness.

11. The surgical cutting block as recited in claim 1, wherein said first surface includes a flat surface.

12. The surgical cutting block as recited in claim 1, wherein said slot is a horizontal slot that extends through said capture.

13. The surgical cutting block as recited in claim 1, wherein said capture includes a forward face extending axially forward of said opposing second surface of said block body.

14. The surgical cutting block as recited in claim 1, wherein said slot includes a width that is at least as wide as said block body.

15. The surgical cutting block as recited in claim 1, comprising a handle that extends from said block body.

16. The surgical cutting block as recited in claim 1, comprising at least one engagement feature that extends from a side of said block body.

17. The surgical cutting block as recited in claim 16, wherein said at least one engagement feature includes an opening for receiving a fastener.

18. A surgical cutting block, comprising:
- a block body comprising at least one posterior cutting guide slot and at least one chamfer cutting guide slot formed through said block body; and
- a capture separate from and magnetically connected to said block body, said capture including a slot that extends from a front face to a rear face across a thickness of said capture.

19. The surgical cutting block as recited in claim 1, wherein a visualization area of said top surface is exposed between said first surface of said block body, which is adapted to face a bone, and a rear face of said capture.

* * * * *